(12) United States Patent
Levy

(10) Patent No.: US 10,383,702 B2
(45) Date of Patent: Aug. 20, 2019

(54) ANGLE PIECE HEAD

(71) Applicant: MICRO MEGA INTERNATIONAL MANUFACTURES, Besancon (FR)

(72) Inventor: Guy-Charles Levy, Marseilles (FR)

(73) Assignee: MICRO MEGA INTERNATIONAL MANUFACTURES, Besancon (FR)

( * ) Notice: Subject to any disclaimer, the term of this patent is extended or adjusted under 35 U.S.C. 154(b) by 0 days.

(21) Appl. No.: 15/524,976

(22) PCT Filed: Nov. 9, 2015

(86) PCT No.: PCT/FR2015/053025
§ 371 (c)(1),
(2) Date: May 5, 2017

(87) PCT Pub. No.: WO2016/071656
PCT Pub. Date: May 12, 2016

(65) Prior Publication Data
US 2017/0348068 A1 Dec. 7, 2017

(30) Foreign Application Priority Data
Nov. 7, 2014 (FR) ...................................... 14 60763

(51) Int. Cl.
*A61C 1/12* (2006.01)
*A61C 5/42* (2017.01)
(Continued)

(52) U.S. Cl.
CPC ................. *A61C 1/12* (2013.01); *A61C 1/07* (2013.01); *A61C 1/148* (2013.01); *A61C 5/42* (2017.02); *F16H 25/186* (2013.01)

(58) Field of Classification Search
CPC .... A61C 1/12; A61C 1/42; A61C 1/07; A61C 1/148; A61C 1/14; A61C 1/141;
(Continued)

(56) References Cited

U.S. PATENT DOCUMENTS

| 4,834,653 A | 5/1989 | Edwardson |
| 5,042,592 A * | 8/1991 | Fisher ................... B25D 11/08 173/109 |

(Continued)

FOREIGN PATENT DOCUMENTS

| EP | 0161196 A1 | 11/1985 |
| EP | 2438884 A1 | 4/2012 |
| FR | 2 477 407 A | 9/1981 |

*Primary Examiner* — Heidi M Eide
*Assistant Examiner* — Mirayda A Aponte
(74) *Attorney, Agent, or Firm* — Craft Chu PLLC; Andrew W. Chu

(57) ABSTRACT

The angle piece head drives an instrument for operating on dental roots and includes a body having a generally cylindrical cavity and an instrument-holding core in the cavity. The core is shaped to receive and hold the instrument and moves axially and pivotally. The instrument-holding core includes a groove having an offset engaging therewith. The offset engages with one or the other of the two edges of the groove such that the rotation thereof transmits an alternating axial movement to the instrument while enabling same to rotate about the axis of the instrument. The groove includes two portions that extend on either side of a median area. For each portion, the height, namely the distance that separates the two edges, increases from the median area to each end of the groove.

9 Claims, 1 Drawing Sheet

(51) Int. Cl.
*F16H 25/18* (2006.01)
*A61C 1/14* (2006.01)
*A61C 1/07* (2006.01)

(58) Field of Classification Search
CPC ......... A61C 1/142; A61C 1/144; A61C 1/145;
A61C 1/147; F16H 25/186; Y10T 408/23
USPC ........ 142/41, 42, 43, 44, 52, 57, 61, 62, 75,
142/118, 122; 451/108, 133, 136, 150,
451/155, 162, 170, 199, 212, 264, 272,
451/305, 320, 377, 392, 421, 425, 426;
173/216, 49, 104, 109, 122, 124, 220;
433/117; 279/2.16, 71, 74, 78, 114, 118,
279/119
See application file for complete search history.

(56) References Cited

U.S. PATENT DOCUMENTS

| | | |
|---|---|---|
| 5,931,672 A | 8/1999 | Postal |
| 2012/0107766 A1 | 5/2012 | Borgshulte |
| 2013/0101958 A1* | 4/2013 | Garcia .................. A61C 1/06 |
| | | 433/122 |

* cited by examiner

ANGLE PIECE HEAD

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to a driving device for an automated endodontic procedure.

2. Description of Related Art Including Information Disclosed Under 37 CFR 1.97 and 37 CFR 1.98.

Various devices have been proposed to automate the endodontic procedure, first by proposing a head for driving cutting instruments via an alternating rotation, of equal amplitude, of these instruments. Failures were observed because, during the significant friction of the blades of the files on the intraductal dentin, the alternating rotating movements were causing fractures of the files engaged in the channel. Other failures were observed, such as false channels in the ductal curves or perforations.

Since instruments have been placed on the market that are manufactured from specific nickel titanium-based metals, the continuous, slow rotation of instruments suitable for cutting has been proposed using counter-angles producing this slow rotation. However, faced with constant failures, in particular instrument fractures on curved channels, automation by partial alternating rotation was once again proposed in documents EP 2,438,884 and US 2012/107766, in the hopes of minimizing the aforementioned drawbacks through the combined use of nickel titanium instruments.

Another alternative was proposed by the present inventor, and is based on a study of the instrumental dynamics during different phases of the endodontic procedure. This research led to patent EP 0,161,196, but above all to publications in specialized journals, for example Information Dentaire dated Jun. 05, 1986 no. 23 under the title: "Etude fondamentale sur le principe de fonctionnement d'un système automatisé" [Fundamental study on the operating principle of an automated system]. The principle consists of allowing an alternating translational movement of variable amplitude based on the resistance encountered by the blades of a file during its axial movement, and above all allowing a helical movement from the translational movement, since the resistance forces encountered by said inclined blades of the file on the walls of the channel drive the rotation of the file. This helical movement will have a more or less pronounced rotation based on the cutting resistance forces of the blades or during the movement of the file. The file should therefore be given rotational freedom during its movement.

To allow both the alternating translational movement of variable amplitude and this rotational freedom simultaneously, a driving head has been proposed including a body provided with a cavity receiving an instrument holder core coupled to driving means making it possible to communicate alternating axial movements thereto, where said instrument holder core is arranged on the one hand so as to allow an alternating movement of the instrument along its longitudinal axis, and on the other hand so as to impart a freedom of rotational movement around said axis to said instrument.

To that end, the driving axis is equipped with an eccentric housed in a slit or groove housed in the cylindrical instrument holder core. This groove has a length smaller than a 180° arc and a height with relatively significant play between the eccentric and one or the other of the upper or lower walls of the groove.

The minimum amplitude of the alternating longitudinal movements corresponding to the eccentricity of the eccentric is set at 0.5 mm and a maximum amplitude corresponding to the eccentricity increased by the value of the play existing between the walls of the groove and the eccentric is, for a play of 0.75 mm, a total of 1.25 mm.

Three types of problems are encountered when using such an assembly:

First, when a Hedstroem file, instrument whose blades are active in traction and inactive on descent, mounted on such a counter-angle, encounters strong resistance during traction for cutting of the intraductal dentin (therefore during raising of the instrument holder core), and the instrument cannot rise, the counter-angle will be driven depthwise, and could exceed the authorized working length if the operator cannot hold back this descent.

Secondly, there is cause to cite the unpleasant impression experienced by patients under certain circumstances, in particular when using a K-type file that encounters an obstacle: brutal shrinkage of the canal lumen, or calcification of this lumen, or when the diameter of the file is inappropriate for the empty ductal space: the tip of the instrument will strike the obstacle or the ductal walls, creating an unpleasant vibration for the patient. Some call this the jackhammer effect.

BRIEF SUMMARY OF THE INVENTION

The present invention aims to resolve the various aforementioned drawbacks by proposing a driving device for a counter-angle, wherein the new design of the instrument holder core makes it possible to act on the movement value of the core during the use of said counter-angle.

According to the invention, the counter-angle head, used to drive an instrument for procedures on dental roots, made up of a body that includes a generally cylindrical cavity in which an instrument holder core, also generally cylindrical, configured to receive and maintain said instrument, moves, axially and by pivoting, said instrument holder core laterally including a groove or slot formed on a circumference portion and with an orientation perpendicular to the axis of said core, in which an eccentric acts that is supported at the end of a rotary shaft, said eccentric being able to cooperate with one or the other of the two edges of said groove or slot, i.e., a driving edge and a return edge, such that its rotation communicates an axial alternating movement to said instrument while leaving it a possibility of rotational movement around the axis of said instrument, and it is essentially characterized in that said groove or slot comprises two parts that extend on either side of a median zone, for each of which the height, i.e., the distance that separates the driving edge and the return edge, increases from said median zone toward each of the ends of said groove or slot.

According to one additional feature of the counter-angle head according to the invention, the height of the groove or slot at each of the two parts is greater than or equal to the value of the diameter of the eccentric increased by twice the value of the eccentricity, while the height of the groove or slot in its median zone is comprised between the height of the groove or slot at each of the ends of said two parts, and the value of the diameter of the eccentric increased by the eccentricity value.

According to another additional feature of the counter-angle head according to the invention, each of the two parts of the groove or slot has an incline relative to a circumference line, the extreme side parts of said groove or slot moving away from the side of the core by which said instrument is maintained.

As a result, the angle formed by the driving edge relative to the circumference line is smaller than that formed by the return edge relative to the same line.

According to another additional feature of the counter-angle head according to the invention, the slope of the side parts of the groove or slot is from 5° to 15° relative to a circumference line.

According to another additional feature of the counter-angle head according to the invention, the slope of the side parts of the groove or slot is determined based on the weight of the core and the instrument that it holds, this slope decreasing at the same time as this weight.

According to another additional feature of the counter-angle head according to the invention, the groove or slot extends over an angular sector greater than or equal to 100°.

If endodontic instruments with a non-round section are used, the latter should be positioned precisely on the counter-angle head, due to the particular movements of said instruments.

Consequently, according to another additional feature of the counter-angle head according to the invention, the connection between the instrument and the instrument holder core is done through maintaining means associated with means for indexing the angular position of said instrument relative to said core.

According to another additional feature of the counter-angle head according to the invention, the indexing means consist of matching cavities.

BRIEF DESCRIPTION OF THE SEVERAL VIEWS OF THE DRAWINGS

The advantages and features of the counter-angle head according to the invention will emerge more clearly from the following description relative to the appended drawing, which shows one non-limiting embodiment thereof.

In the appended drawing.

DETAILED DESCRIPTION OF THE INVENTION

Figure 1:
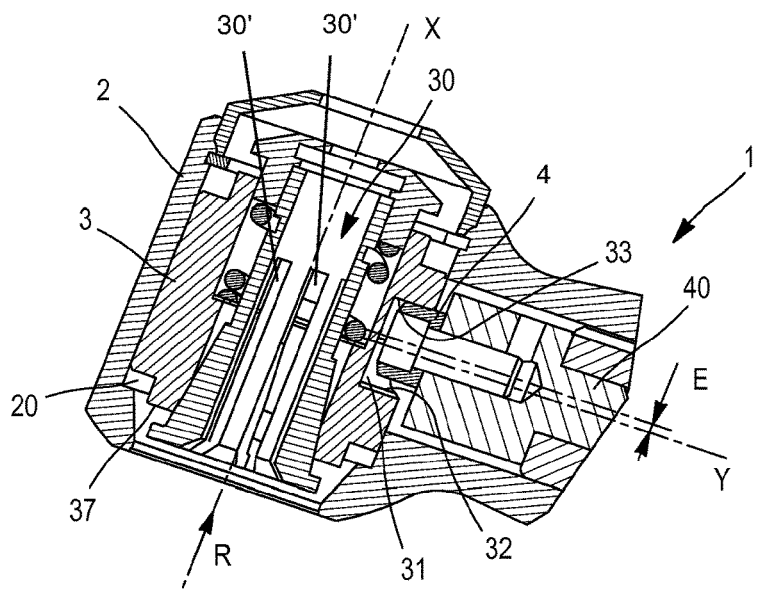
FIG. 1 shows a schematic sectional view along a diametric median plane of a counter-angle head according to the invention.

FIG. 1 shows a counter-angle head 1 according to the invention, which comprises, in a manner known in itself, a body 2 in which a cylindrical cavity 20 is arranged, where an instrument holder core 3 is housed. The core 3 includes means 30 for immobilizing an instrument, not shown, able to maintain said instrument along the axis X of the core 3.

One can see in FIG. 1 that the core 3 includes, on the periphery, in its cylindrical wall as a circumference portion 3', a groove or slot 31 in which an eccentric 4 secured to a rotary shaft 40 can be placed. Under the action of the rotation of the rotary shaft 40 along the axis Y, the eccentric 4, which is off-centered by a value E, alternately comes into contact with a driving edge 32 and a return edge 33 of the groove or slot 31, so as to communicate an alternating axial movement, in directions C and R, respectively, to the core 3 and therefore to the instrument that it holds.

Figure 2:
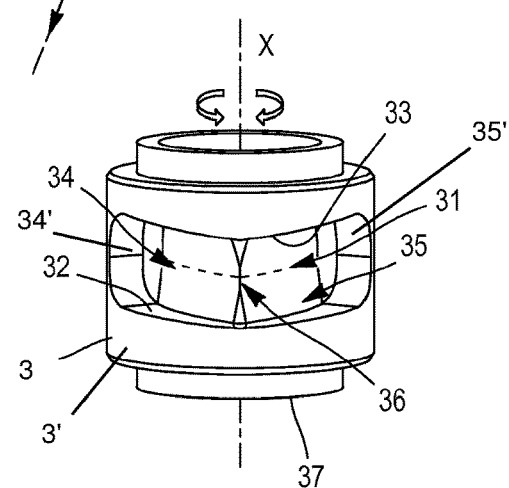
FIG. 2 shows a schematic perspective view of part of the same counter-angle head.
Figure 3:
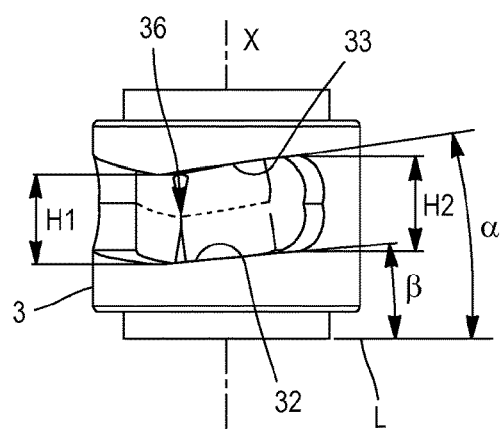
FIG. 3 shows an elevation view of the same part.

FIGS. 2 and 3 show that the groove or slot 31 extends over an angular sector, in the case at hand, non-limitingly, of 120°, and that it includes two parts, a first part 34 having a first part end 34' and a second part 35 having a second part end 35', extending symmetrically on either side of a median zone 36, while describing an incline such that their end moves away from the side 37 of the core 3 from which the instrument protrudes, not shown.

Furthermore, the distance H1 separating the driving edge 32 from the return edge 33 at the median zone 36 is smaller than the distance H2 separating the driving edge 32 from the return edge 33 at each of the ends of the parts 34 and 35.

Note will be made that due to the incline of the parts 34 and 35, the difference in dimensions of H1 and H2 is reflected by the fact that the angle $\alpha$ formed by the return edge 33 of one or the other of the parts 34 and 35 with a circumference line L is larger than the angle $\beta$ formed by the driving edge 32 with the same line. In the case at hand, the angle $\alpha$ is equal to 9°, while the angle $\beta$ is equal to 6°.

That being said, the height H2 is greater than or equal to the value of the diameter of the eccentric 4 increased by twice the eccentricity value E, such that the rotation of the eccentric 4 at the ends of the groove or slot 31 does not create any vibration.

The height H1 is smaller than H2 and larger than the value of the diameter of the eccentric 4 increased by the eccentricity value E.

Thus, as a non-limiting example, the eccentric 4 has a diameter of 2.6 mm, it is off-centered by 0.3 mm, H1 is equal to 2.95 mm and H2 is equal to 3.20 mm, such that a mandatory minimum vibration of 0.2 mm is obtained at the center of the groove or slot 31, at H1, which will decrease the more the eccentric 4 moves toward the ends of one or the other of the parts 34 or 35, to arrive at a mandatory zero movement.

The movement of the core 3 will depend on the frictional forces on the walls of the channel encountered by the endodontic instrument mounted on this core 3.

With low frictional forces, the longitudinal movement of the instrument will have, at H1, a total amplitude corresponding to twice the eccentricity value E, increased by the difference between H1 and the diameter of the eccentric 4 increased by the eccentricity value E.

With increased frictional forces, the pressure of the active elements, blades, of the endodontic instrument on the ductal walls causes the instrument, therefore the core 3, to rotate in the cavity 20, such that the eccentric 4 again acts in zones of the slit or groove 31 where the height is comprised between H1 and H2, and therefore generates a lower, or even zero, amplitude of the movement of the instrument.

Furthermore, over the course of the revolutions of the eccentric, the friction of the blades of the endodontic instrument decreases, and the influence of the helix angle of the blades of the instrument for one rotation of the core lessens. The instrument holder core 3 should then be allowed to return to a zone where the mandatory movement is greater, i.e., a more central zone 36 of the slit or groove 31.

It is with this aim that the slot or groove 31 has a positive slope of its end parts 34 and 35, which may be more or less pronounced based on the weight of the core 3 equipped with the instrument. Thus, very quickly, once the friction of the blades of the endodontic instrument on the walls of the channel disappears, the eccentric 4 regains a more central rotation in the groove or slot 31.

These various implemented methods make it possible to greatly reduce the "jackhammer" effect previously described, and above all, the suction effect of the Hedstroem file when the latter is experiencing strong friction with the walls of the channel.

Furthermore, the operator, through bearing, then traction movements with a low amplitude on the counter-angle, can influence the mandatory vibration amplitude of the file: slight bearing accentuates the pressure of the file on the walls of the channel and causes a low-amplitude mandatory vibration, slight traction makes it possible to extricate the file from overly pronounced friction with a low vibrational amplitude for a low-friction zone allowing a more pronounced vibration.

It will also be noted that in order to reduce the vibration created by the impact of the eccentric 4 on the edges 32 and 33 of the groove or slot 31, the eccentric 4 is trimmed, in the form of a ring 41, for instance, with a shock absorbing material that may for example, non-limitingly, be "Declafor-THX".

It will also be noted that if endodontic instruments with a non-round section, for example ovoid, are used, means are provided for indexing the position of the instrument relative to the core 3, these means preferably assuming the form of matching cavities 30' preferably included by the means 30 and the instrument.

The invention claimed is:

1. A counter-angle head for driving an instrument for procedures on dental roots, said counter-angle head comprises:
  a body being comprised of:
    a cylindrical cavity; and
    an instrument holder core with a core axis, being cylindrical wherein said instrument holder core being moveable axially and by pivoting relative to said cylindrical cavity,
  wherein said instrument holder core is comprised of a circumference portion with a side; and a groove laterally formed on said circumference portion, said groove with an orientation perpendicular to said core axis,
  wherein said groove is comprised of a driving edge and a return edge opposite said driving edge; and
  a rotary shaft with a shaft axis,
  wherein said rotary shaft is comprised of an eccentric supported at an end of said rotary shaft, said eccentric being cooperative with at least one of said driving edge and said return edge, said eccentric is off-center from the shaft axis by an eccentric value,
  wherein rotation of said eccentric around said shaft axis corresponds to the axial movement of said instrument holder core along said core axis in a direction away from said side and in a direction toward said side, said instrument holder core being concurrently rotatable around said core axis,
  wherein said groove defines a median zone with a median zone height corresponding to a distance between said driving edge and said return edge at said median zone,
    wherein said groove defines a first part end and a first part with a first part height corresponding to a distance between said driving edge and said return edge at said first part end, said first part extending between said median zone to said first part end,
    wherein said groove defines a second part end and a second part with a second part height corresponding to a distance between said driving edge and said return edge at said second part end, said second part extending between said median zone to said second part end,
    wherein a distance between said driving edge and said return edge at said median zone increases from said median zone to said first part end,
    wherein a distance between said driving edge and said return edge at said median zone increases from said median zone to said second part end,
    wherein said first part height is greater than or equal to a first value,
    wherein said first value is equal to a diameter of said eccentric increased by twice the eccentricity value of an eccentricity of said eccentric,
    wherein said second part height is greater than or equal to a second value,
    wherein said second value is equal to said first value, and
    wherein said median zone height is a median zone value between said first part height and a third value of said diameter of said eccentric increased by once said eccentricity value of said eccentricity of said eccentric, and between said second part height and said third value of said diameter of said eccentric increased by once said eccentricity value of said eccentricity of said eccentric.

2. The counter-angle head, according to claim 1, wherein said first part is inclined relative to a circumference line, said first part end being angled away from said side of said instrument holder core, and
  wherein said second part is inclined relative to said circumference line, said second part end being angled away from said side of said instrument holder core.

3. The counter-angle head, according to claim 2, wherein said first part is inclined from 5° to 15° relative to said circumference line, and
  wherein said second part is inclined from 5° to 15° relative to said circumference line.

4. The counter-angle head, according to claim 2, wherein said first part is inclined according to weight of said instrument holder core and any instrument assembled to said instrument holder core, and
  wherein said second part is inclined according to said weight of said instrument holder core and any instrument assembled to said instrument holder core.

5. The counter-angle head, according to claim 1, wherein said groove extends over an angular sector greater than or equal to 100°.

6. The counter-angle head, according to claim 1, wherein said eccentric is trimmed with a shock absorbing material.

7. The counter-angle head, according to claim 6, wherein said shock absorbing material is in a ring shape.

8. The counter-angle head, according to claim 1, further comprising: means for indexing angular position relative to said instrument holder core.

9. The counter-angle head, according to claim 8, wherein said means for indexing is comprised of matching cavities.

* * * * *